United States Patent [19]

Manogue et al.

[11] Patent Number: 5,300,713

[45] Date of Patent: * Apr. 5, 1994

[54] HYDROGENOLYSIS OF HALOCARBON MIXTURES

[75] Inventors: William H. Manogue, Newark; V. N. M. Rao, Wilmington, both of Del.

[73] Assignee: E. I. Du Pont de Nemours and Company, Wilmington, Del.

[*] Notice: The portion of the term of this patent subsequent to May 4, 2010 has been disclaimed.

[21] Appl. No.: 998,005

[22] Filed: Dec. 29, 1992

Related U.S. Application Data

[63] Continuation of Ser. No. 682,764, Apr. 9, 1991, Pat. No. 5,208,397.

[51] Int. Cl.$^5$ .................................................. C07C 19/08
[52] U.S. Cl. ................................................ 570/176
[58] Field of Search ....................................... 570/176

[56] References Cited

U.S. PATENT DOCUMENTS

| | | |
|---|---|---|
| 2,005,708 | 6/1935 | Daudt et al. . |
| 2,005,710 | 6/1935 | Daudt et al. . |
| 2,062,748 | 12/1936 | Daudt, et al. . |
| 2,146,725 | 2/1939 | Dunphy . |
| 2,615,926 | 10/1952 | Benning et al. . |
| 2,704,775 | 3/1955 | Clark et al. . |
| 2,748,177 | 5/1956 | Miller et al. . |
| 3,042,727 | 7/1962 | Olstowski et al. . |
| 3,138,559 | 6/1964 | Hauptschein et al. . |
| 4,155,881 | 5/1979 | Sullivan . |
| 4,319,060 | 3/1982 | Cunningham et al. . |
| 5,001,283 | 3/1991 | Fernandez et al. . |

FOREIGN PATENT DOCUMENTS

| | | |
|---|---|---|
| 0349190 | 6/1989 | European Pat. Off. . |
| 0347830 | 12/1989 | European Pat. Off. . |
| 9105752 | 5/1991 | PCT Int'l Appl. . |
| 1578933 | 5/1977 | United Kingdom . |

OTHER PUBLICATIONS

T. Fluorine Chem., 19, pp. 1-20, Gervasutti et al., Received Dec. 12, 1980.

J. Amer. Chem. Soc., 72, pp. 705-707, Miller et al., Feb. 1950.

Primary Examiner—Alan Siegel

[57] ABSTRACT

Mixtures of halocarbons which contain fluorine and chlorine and/or bromine (e.g. a mixture of $CCl_2FCF_3$ with $CClF_2CF_3$, $CCl_2F_2$, $CClF_2CClF_2$ or $CHClF_2$) are contacted with hydrogen in the presence of silicon carbide and/or a metal selected from aluminum, molybdenum, titanium, nickel, iron or cobalt (or their alloys) at temperatures of 350° to 700° C. and pressures of 0 to 1000 psig to obtain a product mixture which substantially corresponds in terms of the distribution of fluorine substituents on carbon atoms with the mixture of halocarbon starting materials.

26 Claims, 1 Drawing Sheet

HYDROGENOLYSIS OF HALOCARBON MIXTURES

This is a continuation of application Ser. No. 07/682,764, filed Apr. 9, 1991 now U.S. Pat. No. 5,208,397.

FIELD OF THE INVENTION

This invention relates to the preparation of halogen substituted hydrocarbons and more particularly to processes for the hydrogenolysis of halocarbons containing fluorine and chlorine and/or bromine.

BACKGROUND OF THE INVENTION

There has been considerable recent interest in halogen substituted hydrocarbons, including a desire to provide effective processes for reducing chlorine and/or bromine content thereof. Hydrogenolysis is a known method for doing this. For example, U.K. Patent 1,578,933 discloses a process for the hydrogenolysis of certain starting materials to tetrafluoroethane using a hydrogenation catalyst (e.g., palladium supported on alumina or carbon). However, as indicated in U.K. Patent 1,578,933 the tetrafluoroethane product produced is dependent to a large extent on the choice of starting materials. When the organic starting material is $CF_3CCl_2F$ (CFC-114a), $CF_3CH_2F$ (HFC-134a) is obtained almost to the exclusion of $CHF_2CHF_2$ (HFC-134); and when the organic starting material is $CClF_2CClF_2$ (CFC-114) the reaction product usually comprises a mixture of the two tetrafluoroethane isomers. Hydrogenolysis can also result in the selective reaction of one isomer in the presence of another. For example, U.S. Pat. No. 4,319,060 discloses a process for the selective hydrogenolysis over a palladium catalyst of CFC-114a in the presence of CFC-114; and describes reacting a feed containing CFC-114 (96–97%) and CFC-114a (3–4%) over Pd/C to produce a mixture containing 95.7 wt. % CFC-114, 2.5 wt. % HFC-134a, 1.0 wt. % HFC-134, and 0.8% of the over-hydrogenated product, $CF_3CH_3$. C. Gervasutti et al., J. Fluorine Chem., 19, 1–20 (1981/82) also discloses the hydrogenolysis of dichlorotetrafluoroethane isomers to tetrafluoroethane isomers, and reports that not only is the symmetric isomer, CFC-114, less reactive than the asymmetric isomer, CFC-114a, but also that some of the CFC-114 isomerizes to CFC-114a under reaction conditions. Thus, in the hydrogenolysis of mixtures of fluorochlorocarbons over a hydrogenation catalyst, selective reaction and isomerization can result in a hydrogenation product mix which is different with respect to the distribution of fluorine substituents on carbon atoms from the mix of reactants. Hydrogenolysis of certain fluorochlorocarbons using tube reactors made of various materials has been disclosed. For example, U.S. Pat. No. 2,615,926 discloses use of platinum tubes, U.S. Pat. No. 2,704,775 disclosed use of nickel and stainless steel tubes and U.S. Pat. No. 3,042,727 discloses use of a Vycor ® tube.

It is desired to provide a process for converting a mixture of halocarbons to a mixture of more hydrogenated halocarbons with high selectivity and particularly to provide such a process wherein formation of solids and plugging of reaction vessels is minimized.

SUMMARY OF THE INVENTION

This invention provides a process for the hydrogenolysis of a mixture of halocarbon starting materials of the formula $C_nH_mF_pX_q$ wherein X is Cl or Br, n is an integer from 1 to 4, m is an integer from 0 to 8, p is an integer from 1 to 9, and q is an integer from 1 to 9 (provided that m+p+q equals 2n+2) wherein the distribution of fluorine substituents on the carbon atoms of a first halocarbon starting material in said mixture is different from the distribution of fluorine substituents on the carbon atoms of a second halocarbon starting material in said mixture. The process employs a reaction vessel (e.g., a tube) of aluminum, molybdenum, titanium, nickel, iron, cobalt, or their alloys, or of silicon carbide, optionally packed with aluminum, molybdenum, titanium, nickel, iron, cobalt or their alloys, or an inert material (e.g., silicon carbide), and comprises contacting the halocarbon mixture with at least 0.5 mole of hydrogen per mole of said halocarbon starting materials in said mixture undergoing hydrogenolysis, at a temperature of 350° to 700° C., and a pressure of 0 to 1000 psig, in the react,ion vessel for a time sufficient to produce a product mixture containing hydrogenolysis product of said first halocarbon starting material wherein at least one X of said first halocarbon starting material has been replaced by a hydrogen atom and the distribution of fluorine substituents on the carbon atoms is the same as the distribution of fluorine substituents on the carbon atoms in said first halocarbon starting material, containing hydrogenolysis product of said second halocarbon starting material wherein at least one X of said second halocarbon starting material has been replaced by a hydrogen atom and the distribution of fluorine substituents on the carbon atoms is the same as the distribution of fluorine substituents on the carbon atoms in said second halocarbon starting material, and having a molar ratio of said hydrogenolysis product of the first halocarbon starting material to said hydrogenolysis product of the second halocarbon starting material substantially equal to the molar ratio of said first halocarbon starting material to said second halocarbon starting material in said mixture of halocarbon starting materials.

DETAILED DESCRIPTION OF THE INVENTION

Figure 1:
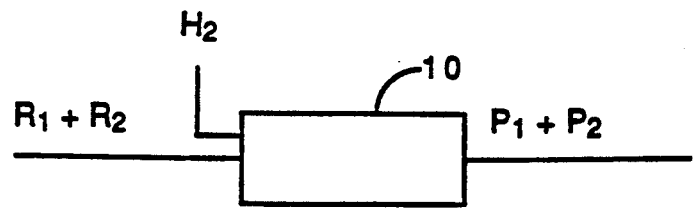
FIG. 1 is a schematic representation of a reactor constructed and operated in accordance with this invention.

This invention provides, a method of producing a mixture of hydrogenolysis products which substantially corresponds (in terms of the distribution of fluorine substituents on carbon atoms) with the mixture of halocarbon starting materials. An important aspect of the present invention is conducting the hydrogenolysis of mixtures of halocarbon starting materials in the presence of silicon carbide, and/or at least one metal selected from aluminum, molybdenum, titanium, nickel, iron, cobalt or their alloys. The metals may be coated on the inside surface of a reaction vessel (e.g., by plating or sputtering the metals or their alloys onto the inside surface). Such coating can help to minimize corrosion of the reaction vessel well. A reaction vessel of these materials (e.g., a metal tube) optionally packed with the metal in suitable form or an inert material such as silica, silicon carbide or low surface area carbon (e.g., shot coke) may also be used. When reference is made to alloys, it is meant a nickel alloy containing from 1 to 99.9% (by weight) nickel, a cobalt alloy containing 1 to 99.9% (by weight) cobalt, an iron alloy containing 0.2 to 99.9% (by weight) iron, a molybdenum alloy containing 70 to 99.9% (by weight) molybdenum, an aluminum alloy containing 80 to 99.9% (by weight) aluminum and a titanium alloy containing 72 to 99.8% (by weight) titanium. Preferably the remainder of these alloys is selected such that the alloy consists essent,ially of (i) one or more metals selected from aluminum, molybdenum, titanium, nickel, iron and cobalt, and optionally (ii) chromium and/or tungsten.

Most preferred for the practice of this invention are nickel or alloys of nickel such as those containing 52% to 80% nickel, e.g., Inconel ® 600 nickel alloy or Hastelloy ® C276 alloy. Included are processes wherein the reaction vessel is either an alloy containing about 76 percent nickel, about 15.5 percent chromium and about 8 percent iron or an alloy containing about 59 percent nickel, about 15.5 percent chromium, about 16 percent molybdenum and about 3.75 percent tungsten; and wherein the reaction vessel is empty or is packed with an alloy containing about 76 percent nickel, about 15.5 percent chromium and about 8 percent iron, or with an alloy containing about 59 percent nickel, about 15.5 percent chromium, about 16 percent molybdenum and about 3.75 percent tungsten.

When used for packing, the metal, alloys or inert material may be particles or formed shapes such as, for example, perforated plates, saddles, rings (e.g., Pall ® rings), wire, screen, chips, pipe, shot, gauze and wool. Although an empty reaction vessel (e.g., an empty tube) may be used, the use of this type of packing material can provide the advantage of minimizing backmixing. These types of packing material can also serve as heat transfer materials. In many embodiments, perforated plates, saddles and rings can be especially useful.

The invention is applicable to the hydrogenolysis of certain halocarbon mixtures. The mixtures comprise two halocarbon starting materials each of which contain 1 to 4 carbon atoms, and can be generically represented by the empirical formula $C_nH_mF_pX_q$, where X is Cl and/or Br, preferably Cl, and n is an integer from 1 to 4, m is an integer from 0 to 8, p is an integer from 1 to 9, and q is an integer from 1 to 9, provided that $m+p+q=2n+2$. One of these two halocarbon starting materials has a distribution of fluorine substituents on carbon atoms that is different from the distribution of fluorine substituents on the carbon atoms of the other. In other words, either the two halocarbon starting materials have a different number of carbon and/or fluorine atoms, or if hydrogen were substituted for each X in each of the two halocarbon starting materials the two resulting compounds would be positional isomers.

In one general embodiment, isomeric halocarbons selected from halocarbons of the above general formula (e.g., $CClF_2CClF_2$ and $CCl_2FCF_3$) and hydrogen are fed into a reactor at the appropriate conditions to remove at least one of the non-fluorine halogens from the starting materials. In all cases, isomerization of the reactor products is minimal (less than 5%).

In another general embodiment, mixtures of non-isomeric halocarbons selected from halocarbons of the above general formula (e.g., $CF_3CCl_2F$ and $CF_3CClF_2$) and hydrogen are fed into a reactor at the appropriate conditions to remove at least one of the non-fluorine halogens from the starting materials. Examples of other non-isomeric halocarbon mixtures include $CCl_2FCF_3$ and $CCl_2F_2$; $CCl_2FCF_3$ and $CHClF_2$; $CCl_2FCF_3$ and $CF_3CCl_2CF_3$; $CClF_2CClF_2$ and $CCl_2F_2$; $CClF_2CClF_2$ and $CHClF_2$; $CClF_2CClF_2$ and $CF_3CClF_2$; $CClF_2CClF_2$ and $CF_3CCl_2CF_3$; $CF_3CCl_2CF_3$ and $CCl_2F_2$; and $CF_3CCl_2CF_3$ and $CHClF_2$.

The halocarbon mixture fed to the reactor may also contain, in addition to the first halocarbon starting material and second halocarbon starting material described above, other halocarbons (which may or may not undergo hydrogenolysis in the reactor), and inert materials such as nitrogen, and hydrocarbons (e.g., $CH_4$ or $C_2H_6$). For example, where the first and second halocarbon starting materials are $CClF_2CClF_2$ and $CCl_2FCF_3$, the mixture of halocarbon starting materials may also contain another halocarbon selected from the group consisting of $CClF_2CF_3$, $CCl_2F_2$, $CHClF_2$ and $CF_3CCl_2CF_3$.

In many useful embodiments the mole ratio of the first halocarbon starting material to the second halocarbon starting material is between 1:99 and 99.1. In some embodiments the mole ratio of the first halocarbon starting material to the second halocarbon starting material is between about 1:9 and 9:1; often between about 1:3 and 3:1.

Preferred embodiments include mixtures wherein the first and second halocarbon starting materials are represented by the formula $C_nH_mF_pX_q$ where n is 2, m is 0, p is 5 and q is 1; where n is 2, m is 0, p is 4, and q is 2; where n is 1, m is 0, p is 2 and q is 2; and/or where n is 1, m is 1, p is 2 and q is 1.

The above halocarbons are either commercially available or can be prepared by known methods or adaptation of known methods.

As previously indicated the first and second halocarbon starting materials when subjected to the process of the invention will result in products wherein one or more X (e.g., chlorine) has been replaced by hydrogen. In accordance with this invention a product mixture is produced which contains (i) hydrogenolysis product of one of said two halocarbon starting materials wherein the distribution of fluorine substituents on the carbon atoms is the same as the distribution of fluorine substituents on the carbon atoms of that first starting material, and (ii) hydrogenolysis product of the second of said two halocarbon starting materials wherein the distribution of fluorine substituents on the carbon atoms is the same as the distribution of fluorine substituents on the carbon atoms of that second starting material.

The products of the hydrogenolysis reaction of the $C_1$ halocarbons preferably contain one or two hydrogen atoms, more preferably one. The products of the hydrogenolysis reactions of the $C_2$ halocarbons preferably contain from one to three hydrogen atoms, more preferably one to two. The $C_3$ halocarbons hydrogenolysis products preferably contain one to five hydrogen atoms, with those containing one to four being more preferred.

The preferred process of this invention does not produce olefins as the major product. This is particularly important for the hydrogenolysis of multicarbon halocarbons where such factors as high olefin production can be of concern. Instead, the major product of the conversion includes hydrogenolysis products wherein at least one X of each of the halocarbon starting materials has been replaced by a hydrogen atom. For example, $CF_3CCl_2F$ can be converted with high selectivity to a hydrogenolysis product consisting primarily of $CF_3CHClF$ and $CF_3CH_2F$ with very little olefin formation. In a preferred embodiment of this invention using halocarbons containing fluorine and chlorine, at least about 90% of the hydrogenolysis products contain the same number of fluorines as the original halocarbon.

In the process of this invention the yield loss to olefins, coupled by-products, hydrocarbons, fragmentation products or carbon is less than 10%. Examples of olefins are products such as $CClF=CCF_2$ or $CF_2=CF_2$ the former of which can be obtained from hydrogenolysis of $CCl_2FCClF_2$ and the latter from hydrogenolysis of $CClF_2CClF_2$. An example of a coupled by-product is $CF_3CF=CFCF_3$ which can be obtained by the hydrogenolysis of $CClF_2CClF_2$. Examples of hydrocarbon products are $CH_4$, $C_2H_6$ and $C_3H_8$ which can be obtained by the hydrogenolysis of $CCl_2F_2$, $CCl_2FCClF_2$ and $CF_3CClFCF_3$ respectively. Examples of fragmentation products are $CF_3H$ and $CH_2F_2$ which can be obtained by the hydrogenolysis of $CF_3CCl_2F$ and its isomer. The process can be operated such that the formation of solids in the reaction vessel is low, thus permitting long-term operation with infrequent plugging.

The reaction temperature can range from 350° C. to 700° C. Preferably the reaction temperature is at least about 400° C. For many reactions, especially hydrogenolysis of mixtures, of halocarbons containing 2 carbons, a temperature of at least about 500° C. is particularly preferred.

The amount of hydrogen contained in the gas stream contacted with the gaseous halocarbons undergoing hydrogenolysis should be at least 0.5 mole per mole of said halocarbons. In general, the amount of hydrogen preferably ranges from 2 to 60 moles per mole of said halocarbons, and more preferably ranges from 10 to 30 moles per mole of said halocarbons. The hydrogen can be fed either in the pure state or diluted with an inert gas, e.g., nitrogen, helium, or argon. Preferably, for high selectivitiee, hydrogen is added in sufficient amounts to provide a reactor effluent containing at least about 0.5 mole percent hydrogen.

The process is operable over a broad range of pressures. Generally atmospheric i.e., 0 psig) or superatmospheric pressures of up to 1000 psig are employed. Preferably the pressure is at least about 25 psig. Included are processes wherein the reactor vessel is empty, the temperature ranges from 400° C. to 700° C. and the pressure is 0 to 500 psig.

The extent of the replacement of halogen by hydrogen increases with reaction time. Reaction times between 0.1 minutes and 25 minutes are preferred. Most preferred are reaction times between 0.2 and 8 minutes.

An important feature of the process of the invention is that through selection of the appropriate metal and process conditions, a desired halocarbon hydrogenolysis product can be obtained as the major product with high selectivity and minimal formation of unwanted by-products. As a result during hydrogenolysis of a mixture of halocarbon starting materials in accordance with this invention, a product mixture may be obtained wherein the molar ratio of the hydrogenolysis product of a first halocarbon starting material, to the hydrogenolysis product of a second halocarbon starting material is substantially equal to the molar ratio of the first halocarbon starting material to the second halocarbon starting material in the mixture of halocarbon starting materials. Although these molar ratios of hydrogenolysis products and of starting materials are substantially equal, factors such as a difference between the sensitivity of the first halocarbon starting material and the sensitivity of the second halocarbon starting material to operating conditions (e.g., temperature) can influence the molar ratio of hydrogenolysis products in the reactor effluent. Nevertheless in accordance with this invention the process conditions may be readily controlled and unreacted starting materials may be recycled if necessary, to provide substantially the same conversion of the first and second halocarbon starting materials. As a result, the molar ratio of hydrogenolysis product of the first halocarbon starting material to the hydrogenolysis product of the second halocarbon starting material is ordinarily within about 10% of the molar ratio of the corresponding halocarbon starting materials.

Preferably the reaction time and temperature are selected to obtain long term (>1000 hours) plug free operation and to provide as the major product of the conversion hydrogenolysis product which retains the fluorine content of the starting halocarbon while at least one X is replaced by hydrogen. In many embodiments the reaction time and temperature are controlled so that at least about 90% of halocarbon converted has the same number of fluorine atoms as the halocarbon starting material. Also, in many embodiments the combined yield losses to olefins, coupled by-products, hydrocarbons, or fragmentation products is less than 10%.

An additional desirable feature is that through a selection of a appropriate reaction vessel and packing (e.g., metals, alloys, or inert materials) and process conditions, the products of the hydrogenolysis can contain in high selectivity just one less chlorine or bromine than was present in the starting material. This is particularly useful when q is 2 or more, and it is desired to obtain a major product of the conversion, hydrogenolysis product which contains chlorine and/or bromine. For example, starting with a one-carbon compound containing two or more chlorine or bromine atoms, products containing just one less chlorine.or bromine can be obtained in high selectivity.

Preferably, at least about 10 percent of said first halocarbon starting material and 10 percent of said second halocarbon starting material are converted to hydrogenolysis product during a single pass through the reactor. Although substantial conversions of said first and second halocarbon starting materials (e.g. about 90% or more of each) can be achieved in a once-through system, higher conversions can also be achieved by recycle of unreacted halocarbons or intermediates in a conventional manner.

The process of this invention can be combined with other processes in various multiunit methods for producing mixtures of halogen substituted hydrocarbons. For example, the multiunit methods may include synthesis of the halocarbon starting materials fed to the hydrogenolysis reactor. The effluent from the hydrogenolysis reactor will contain HX (i.e. HCl or HBr), and may also contain minor amounts of HF and/or olefins. The multiunit methods may also include purification of the effluent from the hydrogenolysis reactor (e.g. to remove olefins) and/or separation of the hydrogenolysis products.

The processes of this invention are considered to be characterized by relativity high activation energies when compared to catalytic hydrogenolysis over conventional Pd/C catalyst. For example, the activation energy for the hydrogenolysis of $CF_3CCl_2F$ over a 0.5% Pd/C catalyst at 167° C. to 200° C. was found to be 14–17 Kcal/mole. The activation energy for the hydrogenolysis of $CF_3CHClF$ over a 0.5% Pd/C catalyst at 249° C. to 288° C. was found to be 22–28 Kcal/mole. In contrast, the activation energies for the hydrogenolysis reactions of these compounds conducted in the reaction vessels of this invention, either empty or packed, were found to be considerably larger as exemplified in Table A.

TABLE A

Activation Energy Data
High Temperature Hydrogenolysis

| Feed | Temp. Range | Packing | Activation Energy (Kcal/mole) |
|---|---|---|---|
| $F114_a$[1] | 450–550° C. | — | 49 ± 3 |
| $F114_x$[2] | 440–600° C. | — | 47 ± 2 |
| $F124$[3] | 510–600° C. | — | 49 ± 7 |
| $F114_x$ | 400–570° C. | shot coke | 35 ± 1 |
| $F114_x$ | 400–500° C. | nickel screen | 34 ± 3 |
| $F124$ | 510–570° C. | Inconel ® screen | 41 ± 3 |
| $F124$ | 520–580° C. | shot coke | 37 ± 1 |

[1] $F114_a = CF_3CCl_2F$
[2] $F114_x = $ Du Pont commercial $CClF_2CClF_2$ containing some $CF_3CCl_2F$
[3] $F124 = CF_3CHClF$ The products of the reaction can be separated and purified by conventional means. The products can be used as solvents, blowing agents, refrigerants and propellants.

Employment of the instant invention is further illustrated by reference to FIG. 1 wherein a halocarbon mixture of two halocarbon starting materials, $R_1$ and $R_2$ are fed along with hydrogen i.e., $H_2$) to a reactor (10) constructed and operated in accordance with this invention. The products of the reaction $P_1$ and $P_2$, respectively represent hydrogenolysis products of $R_1$ and $R_2$, and the molar ratio $P_1:P_2$ is substantially equal to the molar ratio of $R_1:R_2$. It will be evident that where the hydrogenolysis reactivity of $R_1$ and $R_2$ are different, then either the reaction time should be selected to obtain substantially complete hydrogenolysis of $R_1$ and $R_2$ during a single pass through the reactor, or unreacted starting material should be subjected to further hydrogenolysis in accordance with this invention (e.g., by using additional reactors or by recycling unreacted starting material back to reactor (10)).

Figure 2:
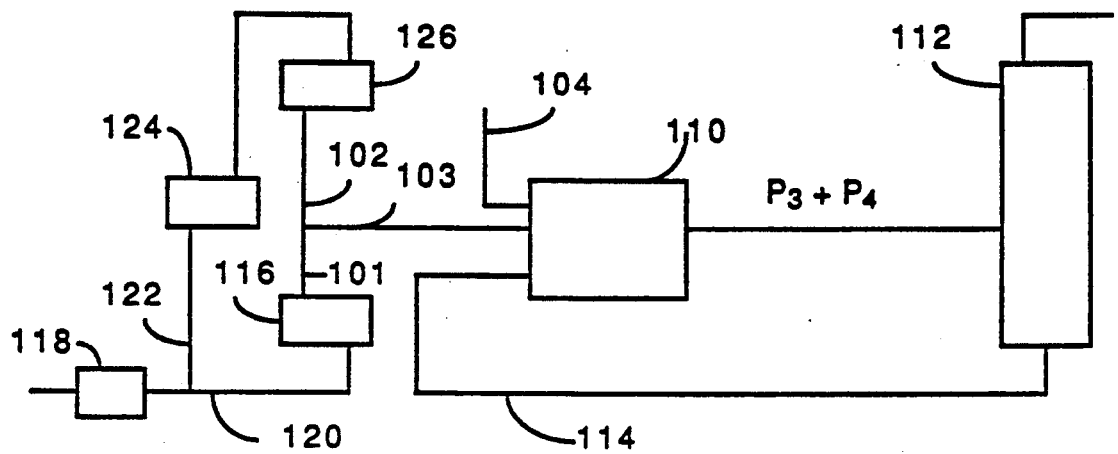
FIG. 2 is a schematic representation of a multiunit process employing a reactor constructed and operated in accordance with this invention.

FIG. 2 illustrates employment of a multiunit method for producing a mixture of $CHF_2CHF_2$ and $CH_2FCF_3$. In the illustrated method a halocarbon mixture of two halocarbon starting materials, $CClF_2CClF_2$ and $CCl_2FCF_3$ from feedline (103) are fed along with hydrogen from feedline (104) to a reactor (110) constructed and operated in accordance with this invention. $P_3$ represents the hydrogenolysis product of $CClF_2CClF_2$ (i.e., $CHF_2CHF_2$ and, if total hydrogenolysis is not achieved, $CClF_2CHF_2$); and $P_4$ represents the hydrogenolysis product of $CCl_2FCF_3$ (i.e., $CH_2FCF_3$ and, if total hydrogenolysis is not achieved, $CHClFCF_3$). The hydrogenolysis products $P_3$ and $P_4$ are fed along with other materials from reactor (110) to a separation system such as distillation column (112), and any unreacted $CClF_2CClF_2$ and/or $CCl_2FCF_3$ is recycled back to the reactor using recycle line (114). In accordance with this invention the molar ratio of $P_3$ to $P_4$ is substantially equal to the molar ratio of $CClF_2CClF_2$ to $CCl_2FCF_3$ fed to the reactor (110) from feedline (103). Moreover, if desired $CClF_2CHF_2$ and $CHClFCF_3$ may be recycled as well, such that the mixture of $CHF_2CHF_2$ and $CH_2FCF_3$ resulting from the process has a molar ratio of $CHF_2CHF_2$ to $CH_2FCF_3$ which is substantially equal to the molar ratio of $CClF_2CClF_2$ to $CCl_2FCF_3$ fed to the reactor (110) from feedline (103).

The $CClF_2CClF_2$ and $CCl_2FCF_3$ fed through feedline (103) may be provided in various ways. For example, a stream containing greater than 75% CFC-114 can be fed to feedline (103) from line (101), a stream containing greater than 75% CFC-114a can be fed to feedline (103) from line (102), and the relative feed rates through lines (102) and (101) can be adjusted.

The streams fed through lines (102) and (101) can be produced in various ways. The $CClF_2CClF_2$-containing material of feedline (101) can be produced in reactor (116) by reacting $CCl_2FCClF_2$ with HF. Reference is made to the vapor phase reaction over a $CrF_3$ alyst disclosed in U.S. Pat. No. 4,155,881. The $CCl_2FCClF_2$ fed to reactor (116) can be produced in reactor (118) by reacting $CCl_2=CCl_2$, $Cl_2$ and HF. Reference is made to the liquid phase reactions of U.S. Pat. No. 2,062,743, U.S. Pat. No. 2,146,725, U.S. Pat. No. 2,005,708 and U.S. Pat. No. 2,005,710 using a $SbCl_5$ catalyst. The $CCl_2FCClF_2$ produced in reactor (118) is fed to reactor (116) through Process line (120). Optionally some of the $CCl_2FCClF_2$ may be fed through process line (122) to isomerization reactor (124) where $CCl_2FCClF_2$ is isomerized to $CCl_3CF_3$. Reference is made to the liquid phase isomerization using an $AlCl_3$ catalyst disclosed in W. T. Miller et al. J. Amer. Chem. Soc. 72 pp 705–707 (1950), and to the vapor phase isomerization using an activated alumina catalyst as disclosed in U.S. Pat. No. 3,138,559. The $CCl_3CF_3$ produced in reactor (124) can be reacted with HF in reactor (126) to produce the $CCl_2FCF_3$-containing material of feedline (102). Reference is made to the liquid phase process disclosed in European Patent Publication No. 349,190 using a $TaCl_5$ catalyst, and to the vapor phase process disclosed in U.S. Pat. No. 2,748,177 using an $AlF_3$ catalyst.

Figure 3:
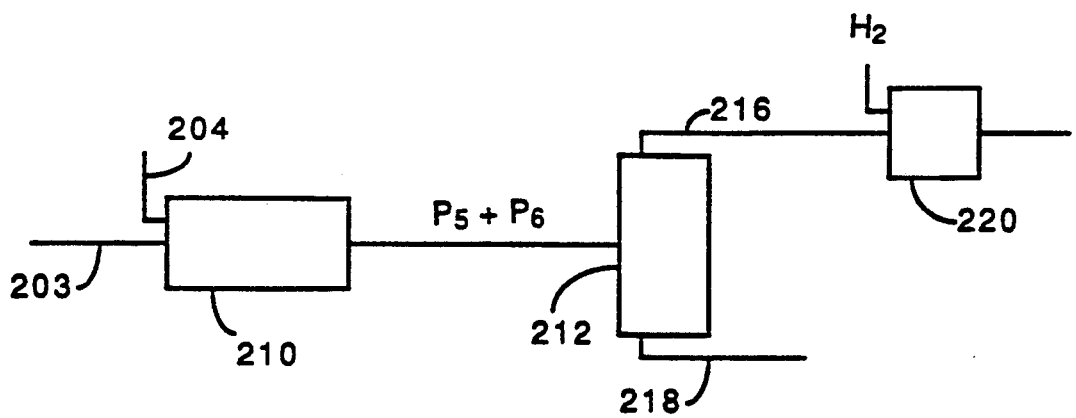
FIG. 3 is a schematic representation of a multiunit process employing a reactor constructed and operated in accordance with this invention.

FIG. 3 illustrates employment of the instant invention in a multiunit method for producing a purified mix of $CHF_2CHF_2$ and $CH_2FCF_3$. In the illustrated method a halocarbon mixture of two halocarbon starting materials, $CClF_2CClF_2$ and $CCl_2FCF_3$ from feedline (203) are fed along with hydrogen from feedline (204) to a reactor (210) constructed and operated in accordance with this invention. $P_5$ represents $CClF_2CHF_2$ and $CHF_2CHF_2$, the hydrogenolysis product of $CClF_2CClF_2$; and $P_6$ represents $CHClFCF_3$ and $CH_2FCF_3$, the hydrogenolysis product of $CCl_2FCF_3$. The reactor may be operated to achieve once-through hydrogenolysis of all $CClF_2CClF_2$ and all $CCl_2FCF_3$. Alternatively, unreacted starting material may be separated from $P_5$ and $P_6$ and recycled. In any case, in accordance with this invention, the molar ratio $P_5: P_6$ is substantially equal to the ratio $CClF_2CClF_2:CCl_2FCF_3$ in the halocarbon mixture (exclusive of recycle) fed to reactor (210). The combined hydrogenolysis products are fed (after removal of most of the excess hydrogen and HCl by-product) to a separation system such as distillation column (212) with a mixture consisting essentially of $CHF_2CHF_2$ and $CH_2FCF_3$ being withdrawn through line (216) and a mixture consisting essentially of $CClF_2CHF_2$ and $CHClFCF_3$ being withdrawn through line (218). The mixture of $C_2H_2F_4$ isomers is treated with hydrogen in reactor (220) to remove any olefinic impurities. The process described in U.S. Pat. No. 5,001,283 may be employed for removal of even relatively small amounts of olefinic materials. Alternatively, a single purification process to remove olefinic impurities may be employed prior to separation.

Practice of the invention will become further apparent from the following non-limiting examples.

EXAMPLES

In the following examples the following general procedure was employed, unless otherwise indicated.

General Procedure

A flow reactor under microprocessor control was used. The reactor was a ⅜-inch by 15-inch Hastelloy® C276 nickel alloy U-tube flow reactor operated at a pressure of 300 psig, immersed in a fluidized sandbath and heated to temperatures of up to 650° C. Hastelloy® C 276 is a commercial alloy containing 59% nickel, 15.5% chromium, 16% molybdenum and 3.75% tungsten.

Hydrogen gas was metered into the system through mass flow controllers. Liquid halocarbons were fed from a syringe pump and vaporized before entering the reactor. Conversions and yields were measured by taking gas stream samples into a gas chromatograph. Product identification was by gc retention times with off-line sampling by gc/mass-spec and gc/ir to confirm peak identification.

The examples demonstrate a single-pass hydrogenolysis and report only major hydrogenolysis products and unreacted starting materials. One skilled in the art will recognize that unreacted starting materials can be separated from the reaction products and recycled in accordance with this invention; and that intermediate products (i.e. products containing Cl) may also be recycled for further hydrogenolysis.

EXAMPLE 1

Hydrogenolysis of CFC-114a/CFC-115 Mixtures $$CF_3CClF_2 + CF_3CCl_2F + H_2 \rightarrow CF_3CHF_2 + CF_3CH_2F + CF_3CHClF + HCl$$

Mixtures of CFC-114a, chloropentafluoroethane (CFC-115) and hydrogen were fed to a reactor operated at several temperatures for 93 hours. For a 10.5 hour period at 650° C., at an average time in synthesis of 37 hours, with liquid feed rates of 6.1 mL/hr of CFC-114a and 0.7 mL/hr of CFC-115 and a hydrogen feed rate of 260 cc/min (1 atm. and room temperature basis); a molar ratio of (CFC-114a+CFC-115):$H_2$ equal to 1:11 was provided, and the organic component of the reactor effluent contained an average (area percent) of 4.09% pentafluoroethane (HFC-125), 0.35% (CFC-115), 86.1% HFC-134a, 6.76% HCFC-124 and less than 0.1% CFC-114a. At 600° C. and the same feed rates, for a 10.5 hour period at an average time in synthesis of 61 hours, the organic composition of the reactor effluent was 2.50% HFC-125, 1.62% CFC-115, 54.7% HFC-134a, 40.0% HCFC-124 and 0.41% CFC-114a.

EXAMPLE 2

Hydrogenolysis of CFC-114a/CFC-12 Mixtures $$CCl_2F_2 + CF_3CCl_2F + H_2 \rightarrow CH_2F_2 + CHClF_2 + CF_3CH_2F + CF_3CHClF + HCl$$

Mixtures of 2,2-dichloro-1,1,1,2-tetrafluoroethane (CFC-114a), dichlorodifluoromethane (CFC-12) and hydrogen were fed to a reactor operated at several temperatures for 92 hours. For a 10.5 hour period at 600° C., at an average time in synthesis of 38 hours, with liquid feed rates of 11.9 mL/hr of CFC-114a and 1.2 mL/hr of CFC-12 and a hydrogen feed rate of 500 cc/min (1 atm. and room temperature basis); a molar ratio of (CFC-114a+CFC-12):$H_2$ equal to 1:11 was provided, and the organic component of the reactor effluent contained an average (area percent) of 0.97% difluoromethane (HFC-32), 1.57% chlorodifluoromethane (FCFC-22), and 0.25% CFC-12, as well as 37.7% HFC-134a, 56.0% HCFC-124 and 2.8% CFC-114a.

The temperature was lowered to 550° C. For a 6 hour period at an average time in synthesis of 55 hours, the average organic component of the reactor effluent was 0.71% HFC-32, 1.28% HCFC-22, 2.21% CFC-12, 4.22% HFC-134a, 49.0% HCFC-124 and 42.8% CFC-114a.

EXAMPLE 3

Hydrogenolysis of CFC-114a/CFC-114 Mixtures $$CF_3CCl_2F + CClF_2CClF_2 + H_2 \rightarrow CF_3CHClF + CHF_2CClF_2 + CF_3CH_2F + CHF_2CHF_2 + HCl$$

Various mixtures of 2,2-dichloro-1,1,1,2-tetrafluoroethane (CFC-114a) and 1,2-dichloro-1,1,2,2-tetrafluoroethane (CFC-114) and hydrogen were fed to the reactor for a period of 170 hours. For an 11 hour period at 600° C., at an average time in synthesis of 50 hours, with a feed molar ratio of hydrogen to CFC-114/114a isomers of 11:1, and a liquid feed rate of 13.2 mL/hr of an equal mixture of the 2,2-dichloro and the 1,2-dichloro isomers, the average conversion of the 2,2-dichloro isomer was 98% and the average conversion of the 1,2-dichloro isomer was 80%. The reactor effluent contained in addition to HCl and $H_2$ 1.36% HFC-134, 0.67% HCFC-124a and 0.68% CFC-114, as well as 1.34% HFC-134a, 2.04% HCFC-124 and 0.06% CFC-114a.

For a 13.5 hour period at 600° C., at an average time in synthesis of 115 hours, with a feed molar ratio of hydrogen to CFC-114a/114 isomers of 11:1, and a liquid feed rate of 3 mL/hr of a 11/1 mixture of CFC-114a/114, the average conversion of CFC-114a was 100% and the average conversion of CFC-114 was 96%. The reactor effluent contained in addition to HCl and $H_2$, 4.35% HFC-134a, 1.35% HCFC-124 and less than 0.1% CFC-114a as well as 0.153% HFC-134, 0.066% HCFC-124a and 0.15% CFC-114.

EXAMPLE 4

Hydrogenolysis of CFC-114a/HCFC-22 Mixtures $$CF_3CCl_2F + CHClF_2 + H_2 \rightarrow CF_3CH_2F + CF_3CHClF + CH_2CF_2 + HCl$$

Mixtures of CFC-114a, HCFC-22 and hydrogen were fed to a reactor operated at several temperatures for 40 hours. For a 10.5 hour period at 600° C., at an average time in synthesis of 14 hours, with liquid feed rates of 5.5 mL/hr of CFC-114a and 1 mL/hr of HCFC-22, a hydrogen feed rate of 250 cc/min (1 atm. and room temperature basis); a molar ratio of hydrogen to (HFC-114 at HCFC-22) of 10:1 was provided, and the organic component of the reactor effluent contained an average (area percent) of 51.6% HFC-134a, 35.6% HCFC-124, 0.22% CFC-114a, 4.1% HFC-32 and 5.4% HCFC-22.

EXAMPLE 5

Hydrogenolysis of CFC-114a/CFC-114 Mixtures

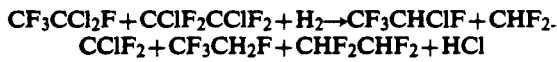

A mixture containing about 8% 2,2-dichloro-1,1,1,2-tetrafluoroethane (CFC-114a) and about 92% 1,2-dichloro-1,1,2,2-tetrafluoroethane (CFC-114) and hydrogen were fed to the reactor for a period of 477 hours. For an 11 hour period at 470° C., at an average time in synthesis of 67 hours, with a feed molar ratio of hydrogen to CFC-114/114a isomers of 2.1:1, and a liquid feed rate of 2.0 mL/hr of the combined 2,2-dichloro and the 1,2-dichloro isomers, the average conversion of the 2,2-dichloro isomer was 86% and the average conversion of the 1,2-dichloro isomer was 48. The reactor effluent contained in addition to HCl and hydrogen, 2.3% HFC-134, 10.2% HCFC-124a and 13.9% CFC-114, as well as 0.4% HFC-134a, 1.6% HCFC-124 and 0.3% CFC-114a.

EXAMPLE 6

Hydrogenolysis of CFC-114a/CFC-114 Mixtures

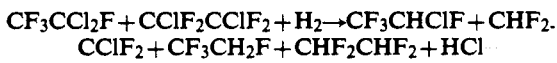

A mixture containing about 8% 2,2-dichloro-1,1,1,2-tetrafluoroethane (CFC-114a) and about 92% 1,2-dichloro-1,1,2,2-tetrafluoroethane (CFC-114) and hydrogen were fed to the reactor for a period of 477 hours. For an 3 hour period at 560° C., at an average time in synthesis of 275 hours, with a feed molar ratio of hydrogen to CFC-114/114a isomers of 2.2:1, and a liquid feed rate of 1.0 mL/hr of the combined 2,2-dichloro and the 1,2-dichloro isomers, the average conversion of the 2,2-dichloro isomer was 96% and the average conversion of the 1,2-dichloro isomer was 92%. The reactor effluent contained in addition to HCl and hydrogen, 17.4% HFC-134, 4.5% HCFC-124a and 2.0% CFC-114, as well as 2.0% HFC-134a, 0.5% HCFC-124 and 0.1% CFC-114a.

Particular embodiments of the invention are included in the examples. Other embodiments will become apparent to those skilled in the art from a consideration of the specification or practice of the invention disclosed herein. It is understood that modifications and variations may be practiced without departing from the spirit and scope of the novel concepts of this invention. It is further understood that the invention is not confined to the particular formulations and examples herein illustrated, but it embraces such modified forms thereof as come within the scope of the following claims.

What is claimed is:

1. A process for the hydrogenolysis of a mixture of halocarbon starting materials having the formula $C_nH_mF_pX_q$ wherein X is Cl or Br, n is an integer from 2 to 4, m is an integer from 0 to 8, p is an integer from 1 to 9, and q is an integer from 1 to 9 provided that $m+p+q$ equals $2n+2$, wherein the distribution of fluorine substituents on the carbon atoms of a first halocarbon starting material in said mixture is different from the distribution of fluorine substituents on the carbon atoms of a second halocarbon starting material in said mixture, comprising the step of: contacting said mixture with at least 0.5 mole of hydrogen per mole of said halocarbon starting materials in said mixture undergoing hydrogenolysis, in a reaction vessel of aluminum, molybdenum, titanium, nickel, iron, cobalt, or their alloys or of silicon carbide, which is either empty or is packed with particles or formed shapes of aluminum, molybdenum, titanium, nickel, iron, cobalt, or their alloys or silicon carbide or low surface area carbon at a pressure within the range of from 0 psig to 1000 psig, at a temperature within the range of from 500° C. to 700° C. and for a time sufficient to produce a product mixture containing hydrogenolysis product of said first halocarbon starting material wherein at least one X of said first halocarbon starting material has been replaced by a hydrogen atom and the distribution of fluorine substituents on the carbon atoms is the same as the distribution of fluorine substituents on the carbon atoms in said first halocarbon starting material, containing hydrogenolysis product of said second halocarbon starting material wherein at least one X of said second halocarbon starting material has been replaced by a hydrogen atom and the distribution of fluorine substituents on the carbon atoms is the same as the distribution of fluorine substituents on the carbon atoms in said second halocarbon starting material, and having a molar ratio of said hydrogenolysis product of the first halocarbon starting material to said hydrogenolysis product of the second halocarbon starting material substantially equal to the molar ratio of said first halocarbon starting material to said second halocarbon starting material in said mixture of halocarbon starting materials; said molar ratio of said first halocarbon starting material to said second halocarbon starting material being between about 1:99 and 99:1.

2. The process of claim 1 wherein the first and second halocarbon starting materials are $CF_3CCl_2F$ and $CF_3CClF_2$.

3. The process of claim 2 wherein the reaction vessel is empty.

4. The process of claim 2 wherein the reaction vessel is nickel or a nickel alloy and is either empty or packed with nickel or a nickel alloy.

5. The process of claim 4 wherein the reaction vessel is empty.

6. The process of claim 1 wherein the first and second halocarbon starting materials are $CClF_2CHF_2$ and $CHClFCF_3$.

7. The process of claim 6 wherein the reaction vessel is empty.

8. The process of claim 6 wherein the reaction vessel is nickel or a nickel alloy and is either empty or packed with nickel or a nickel alloy.

9. The process of claim 8 wherein the reaction vessel is empty.

10. The process of claim 1 wherein the first and second halocarbon starting materials are $CClF_2CClF_2$ and $CF_3CClF_2$.

11. The process of claim 10 wherein the reaction vessel is empty.

12. The process of claim 10 wherein the reaction vessel is nickel or a nickel alloy and is either empty or packed with nickel or a nickel alloy.

13. The process of claim 12 wherein the reaction vessel is empty.

14. The process of claim 11 wherein the reaction vessel is empty.

15. The process of claim 1 wherein the first and second halocarbon starting materials are $CF_3CCl_2F$ and $CClF_2CClF_2$.

16. The process of claim 15 wherein the $CClF_2CClF_2$ is produced by reaction of $CClF_2CCl_2F$ with HF.

17. The process of claim 16 wherein the $CClF_2CClF_2$ is produced by the reaction of $CCl_2=CCl_2$, $Cl_2$ and HF.

18. The process of claim 15 wherein substantially complete hydrogenolysis of $CF_3CCl_2F$ and $CClF_2CClF_2$ is obtained during a single pass through the reactor.

19. The process of claim 15 wherein $CF_3CHClF$ is produced by the hydrogenolysis and is recycled.

20. The process of claim 15 wherein the hydrogenolysis produces a mixture of $CF_3CH_2F$ and $CHF_2CHF_2$ containing olefinic impurities, and wherein the said mixture of $CF_3CH_2F$ and $CHF_2CHF_2$ is treated with hydrogen to remove the olefinic impurities.

21. The process of claim 15 wherein the reaction vessel is nickel or nickel alloy and is either empty or packed with nickel or nickel alloy.

22. The process of claim 21 wherein the reaction vessel is empty.

23. The process of claim 1 wherein the mixture fed to the reactor contains inert materials.

24. The process of claim 1 wherein the mixture fed to the reactor contains $N_2$.

25. The process of claim 1 wherein the mixture fed to the reactor contains other halocarbons which do not undergo hydrogenolysis in the reactor.

26. The process of claim 1 wherein the reaction vessel is nickel or nickel alloy and contains perforated plates of nickel or nickel alloy.

* * * * *